US011480560B2

(12) United States Patent
Benam et al.

(10) Patent No.: US 11,480,560 B2
(45) Date of Patent: Oct. 25, 2022

(54) DELIVERY OF AEROSOLIZED RESPIRATORY PATHOGENS

(71) Applicant: THE REGENTS OF THE UNIVERSITY OF COLORADO, A BODY CORPORATE, Denver, CO (US)

(72) Inventors: Kambez Hajipouran Benam, Denver, CO (US); Brian Frazier Niemeyer, Denver, CO (US); Alexander Joseph Kaiser, Keenesburg, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 152 days.

(21) Appl. No.: 16/438,092

(22) Filed: Jun. 11, 2019

(65) Prior Publication Data
US 2019/0376950 A1 Dec. 12, 2019

Related U.S. Application Data

(60) Provisional application No. 62/683,522, filed on Jun. 11, 2018.

(51) Int. Cl.
*C12M 1/00* (2006.01)
*G01N 33/50* (2006.01)
(Continued)

(52) U.S. Cl.
CPC ........ *G01N 33/5005* (2013.01); *C12M 21/08* (2013.01); *C12M 29/10* (2013.01);
(Continued)

(58) Field of Classification Search
CPC ...... C12M 25/10; C12M 29/10; C12M 29/20; C12M 33/14; C12M 21/08; G01N 33/5005; G01N 33/56983
See application file for complete search history.

(56) References Cited

U.S. PATENT DOCUMENTS 4,649,911 A 3/1987 Knight et al.
8,281,641 B1 * 10/2012 Wooten .................. A62B 27/00
73/1.68
(Continued)

FOREIGN PATENT DOCUMENTS

CN 106635954 5/2017
WO 2007119073 10/2007
(Continued)

OTHER PUBLICATIONS

Non-Final Office Action dated Oct. 15, 2021 in U.S. Appl. No. 16/648,854.
(Continued)

*Primary Examiner* — Jonathan M Hurst
(74) *Attorney, Agent, or Firm* — Snell & Wilmer L.L.P.

(57) ABSTRACT

A system comprising a respirator, a biochip, and an atomizer for studying respiratory pathogens. The respirator of the system is configured to create breathe-mimicking air movement, the biochip comprises an airway lumen in fluid communication with the respirator, and the atomizer is in fluid communication with the airway lumen of the biochip, according to various embodiments. The atomizer may be configured to generate droplets of a respiratory pathogen (e.g., from liquid inoculum). In various embodiments, the breath-mimicking air movement comprises air volume as a function of time, wherein the respirator is configured to generate breathing cycles.

17 Claims, 6 Drawing Sheets

(51) Int. Cl.
    *G01N 33/569*    (2006.01)
    *C12M 1/26*     (2006.01)
    *C12M 3/00*     (2006.01)

(52) U.S. Cl.
    CPC ............ *C12M 29/20* (2013.01); *C12M 33/14* (2013.01); *G01N 33/56983* (2013.01)

(56) References Cited

U.S. PATENT DOCUMENTS

| | | | |
|---|---|---|---|
| 8,647,410 | B2 | 2/2014 | Borenstein et al. |
| 8,647,861 | B2 | 2/2014 | Ingber et al. |
| 2006/0156978 | A1 | 7/2006 | Lipson et al. |
| 2006/0195179 | A1 | 8/2006 | Sun et al. |
| 2011/0033887 | A1 | 2/2011 | Fang et al. |
| 2011/0086382 | A1 | 4/2011 | Marx |
| 2011/0250585 | A1 | 10/2011 | Ingber et al. |
| 2011/0250688 | A1 | 10/2011 | Hasan |
| 2014/0057311 | A1 | 2/2014 | Kamm et al. |
| 2014/0158233 | A1 | 6/2014 | Leslie et al. |
| 2014/0335496 | A1* | 11/2014 | Grego ............... G09B 23/306 434/272 |
| 2014/0342445 | A1 | 11/2014 | Ingber et al. |
| 2014/0352689 | A1* | 12/2014 | Seshadri ........... A61M 15/0028 128/200.16 |
| 2015/0004077 | A1* | 1/2015 | Wikswo ............. G01N 33/5082 422/502 |
| 2015/0240194 | A1 | 8/2015 | Neumann et al. |
| 2015/0377861 | A1 | 12/2015 | Pant et al. |
| 2016/0068793 | A1 | 3/2016 | Maggiore |
| 2016/0074558 | A1 | 3/2016 | Murphy et al. |
| 2016/0167051 | A1 | 6/2016 | Collins |
| 2016/0313306 | A1* | 10/2016 | Ingber .................... C12M 25/02 |
| 2017/0198252 | A1 | 7/2017 | Mironov et al. |
| 2017/0355153 | A1 | 12/2017 | Albert et al. |
| 2017/0355940 | A1 | 12/2017 | Neumann et al. |
| 2018/0085493 | A1 | 3/2018 | Lee |
| 2018/0106784 | A1 | 4/2018 | Sears et al. |
| 2018/0110901 | A1 | 4/2018 | Lewis |
| 2018/0326665 | A1 | 11/2018 | Gatenholm |

FOREIGN PATENT DOCUMENTS

| | | | |
|---|---|---|---|
| WO | 2012154834 | | 11/2012 |
| WO | WO-2012154834 A1 * | 11/2012 | ............ C12M 29/14 |
| WO | 2013086486 | | 6/2013 |
| WO | 2013086502 | | 6/2013 |
| WO | 2013155513 | | 10/2013 |
| WO | WO-2013155513 A1 * | 10/2013 | ......... B05B 11/3028 |
| WO | 2015138034 | | 9/2015 |
| WO | 2016164566 | | 10/2016 |
| WO | 2016179242 | | 11/2016 |
| WO | 2017019778 | | 2/2017 |
| WO | 2017040675 | | 3/2017 |

OTHER PUBLICATIONS

Final Office Action dated Feb. 25, 2022 in U.S. Appl. No. 16/648,854.
Advisory Action dated May 2, 2022 in U.S. Appl. No. 16/648,854.
Non-Final Office Action dated Jun. 14, 2022 in U.S. Appl. No. 16/648,854.
PCT; International Search Report and Written Opinion dated Dec. 12, 2018 in Application No. PCT/US2018/052166.
PCT; International Preliminary Report on Patentability dated Mar. 24, 2020 in Application No. PCT/US2018/052166.
Non-Final Office Action dated Mar. 16, 2022 in U.S. Appl. No. 16/967,395.
PCT; International Search Report and Written Opinion dated Apr. 15, 2019 in Application No. PCT/US2019/017540.
PCT; International Preliminary Report on Patentability dated Aug. 11, 2020 in Application No. PCT/US2019/017540.
Huh, D et al. "From Three-Dimensional Cell Culture to Organs-on-Chips" Trends Cell Biology, Dec. 7, 2011; vol. 21 Issue 12: pp. 745-754.doi:10.1016/j.tcb.2011.09.005.
Ozbolat et al., "Bioprinting toward organ fabrication: challenges and future trends," IEEE Transactions on Biomedical Engineering, vol. 60, 3, pp. 691-699 (2013).
Bajaj et al. "3D biofabrication strategies for tissue engineering and regenerative medicine," Annual Review Biomed Engineering, pp. 247-276 (2014).
Landers et al., "Fabrication of soft tissue engineering scaffolds by means of rapid prototyping techniques," Journal of Materials Science, 37, pp. 3107-3116 (2002).
Melchels et al., "Additive manufacturing of tissues and organs," School of Engineering & Physical Sciences, Institute of Biological Chemistry, Biophysics and Bioengineering, vol. 37, pp. 1079-1104 (2012).
Gesim Bioinstruments and Microfluids, https://gesim-bioinstruments-microfluidics.com/. Accessed on: Aug. 4, 2020.
There's Only One 3D-Bioplotter. https://envisiontec.com/3d-printers/3d-bioplotter/. Accessed on: Aug. 4, 2020.
Bioprinter Fabion. https://bioprinting.ru/en/products-services/fabion/. Accessed on: Aug. 4, 2020.
Cyfuse Regenova. https://www.cyfusebio.com/en/product/3dprinter/device/. Accessed on: Aug. 4, 2020.
Cyfuse S-Pike. https://www.cyfusebio.com/en/product/3dprinter/spike/. Accessed on: Aug. 4, 2020.
Aspect Biosystems, https://www.aspectbiosystems.com/technology. Accessed on: Aug. 4, 2020.
BioAssemblybot. https://www.advancedsolutions.com/bioassemblybot. Accessed on: Aug. 4, 2020.
Organovo Technology Platform, https://organovo.com/technology-platform/. Accessed on: Aug. 4, 2020.
Regenhu Biosystem Architects—3DDiscovery Evolution, https://www.regenhu.com/3d-bioprinters. Accessed on: Aug. 4, 2020.
BioBotBasic. https://www.advancedsolutions.com/biobot. Accessed on: Aug. 4, 2020.
Allevi—Compare Bioprinters, https://www.allevi3d.com/compare/. Accessed on: Aug. 4, 2020.
Aether, https://discoveraether.com/. Accessed on: Aug. 4, 2020.
Cellink Life Sciences, https://www.cellink.com/. Accessed on: Aug. 4, 2020.
Non-Final Office Action dated Mar. 25, 2021 in U.S. Appl. No. 16/438,092.
Final Office Action dated Dec. 17, 2021 in U.S. Appl. No. 16/438,092.
Advisory Action dated Mar. 11, 2022 in U.S. Appl. No. 16/438,092.

\* cited by examiner

DELIVERY OF AEROSOLIZED RESPIRATORY PATHOGENS

CROSS-REFERENCE TO RELATED APPLICATIONS

This application claims priority to, and the benefit of, U.S. provisional patent application Ser. No. 62/683,522 filed Jun. 11, 2018 and entitled "Delivery of Aerosolized Respiratory Pathogens," the entire contents of which are incorporated herein by reference in their entirety for all purposes.

FIELD

The present disclosure relates to the study of respiratory pathogens, and more specifically to apparatuses, systems, and methods for inhaled delivery of aerosolized respiratory pathogens.

BACKGROUND

Current platforms to study in vitro or ex vivo respiratory pathogens, including viruses, using human and non-human cells/tissues often face a common problem: inability to accurately recreate clinically relevant physiological exposure to the pathogen. The most widely used protocols to study lung viral infections, as representative pulmonary pathogens, require that the cells be submerged in a liquid inoculum containing the virus. However, humans are NOT normally exposed to respiratory viruses by taking in large volumes of a liquid that contain the virus, which would disrupt the air-liquid interface (ALI) that naturally exists in our lungs. Instead, but humans typically inhale air (under physiological rhythmic breathing) containing aerosolized viral particles, thereby contracting the infection. Accordingly, conventional modeling systems do not accurately mimic physiologically relevant and clinically significant exposure to inhaled pathogens. That is, using liquid inoculums in conventional infection protocols not only disrupts the air-liquid interface that would exist in vivo, but also fails to recapitulate the mechanical forces associated with air shear during physiological breathing.

SUMMARY

Disclosed herein, according to various embodiments, is a system comprising a respirator, a biochip, and an atomizer. The respirator is configured to create breathe-mimicking air movement; the biochip comprises an airway lumen in fluid communication with the respirator, and the atomizer is in fluid communication with the airway lumen of the biochip, according to various embodiments.

The atomizer may be configured to generate droplets of a respiratory pathogen (e.g., from liquid inoculum). In various embodiments, the breath-mimicking air movement comprises air volume as a function of time, wherein the respirator is configured to generate breathing cycles. The respirator may be a pneumatic extruder comprising at least one syringe, wherein the at least one syringe comprises a plunger configured to translate linearly to produce the breathe-mimicking air movement.

In various embodiments, the airway lumen of the biochip is lined with primary mucociliated human lung airway epithelial cells. In various embodiments, the biochip comprises a plurality of continuously perfused hollow microchannels inhabited by living tissue cells arranged to simulate organ-level physiology. In various embodiments, the airway lumen of the biochip comprises a circular cross-section. The biochip may also include a vascular channel and a membrane disposed between the airway lumen and the vascular channel. In various embodiments, a width of the membrane is less than 1,000 micrometers, and may be less than 500 micrometers. In various embodiments, a first end of the airway lumen of the biochip is coupled to the respirator and a second end of the airway lumen of the biochip is coupled to the atomizer.

In various embodiments, the atomizer comprises an atomizing membrane, such as an electronically actuated piezoelectric atomizer. In various embodiments, the atomizer comprises a housing comprising a lower compartment defining a reservoir for liquid inoculum, an upper compartment defining a volume for generated aerosols, and at least one sample port for fluidly connecting the upper compartment to at least one of the biochip and the respirator. The atomizing membrane may be disposed between the lower compartment and the upper compartment. In various embodiments, the atomizer further comprises a support stand disposed in the lower compartment and configured to support the atomizing membrane. The atomizer may further include a capillary tube attached to a microscale-inner-diameter flexible polymer tubing configured to receive liquid inoculum. The upper compartment defines an access port through which the support stand may be inserted, according to various embodiments. The atomizer may also include an air filter configured to vent the system. Also, the system may include a pump configured to deliver liquid inoculum to the atomizer.

The forgoing features and elements may be combined in various combinations without exclusivity, unless expressly indicated herein otherwise. These features and elements as well as the operation of the disclosed embodiments will become more apparent in light of the following description and accompanying drawings.

DETAILED DESCRIPTION

Disclosed herein, according to various embodiments, is a novel system described here (FIG. 1) that is a multi-compartment platform comprising of three main components: (1) a sealable electrotechnical atomization chamber to generate aerosolized viral (or any other pathogenic) particles for inhalation exposure to living lung cells/tissue/organ without disrupting natural ALI, (2) a programmable biochip microrespirator to mimic physiological breathing airflows, and (3) a lung organomimetic Organ-on-a-Chip (referred hereon as 'biochip') that contains human airway epithelial cells for exposure to inhaled microbe.

Figure 1:
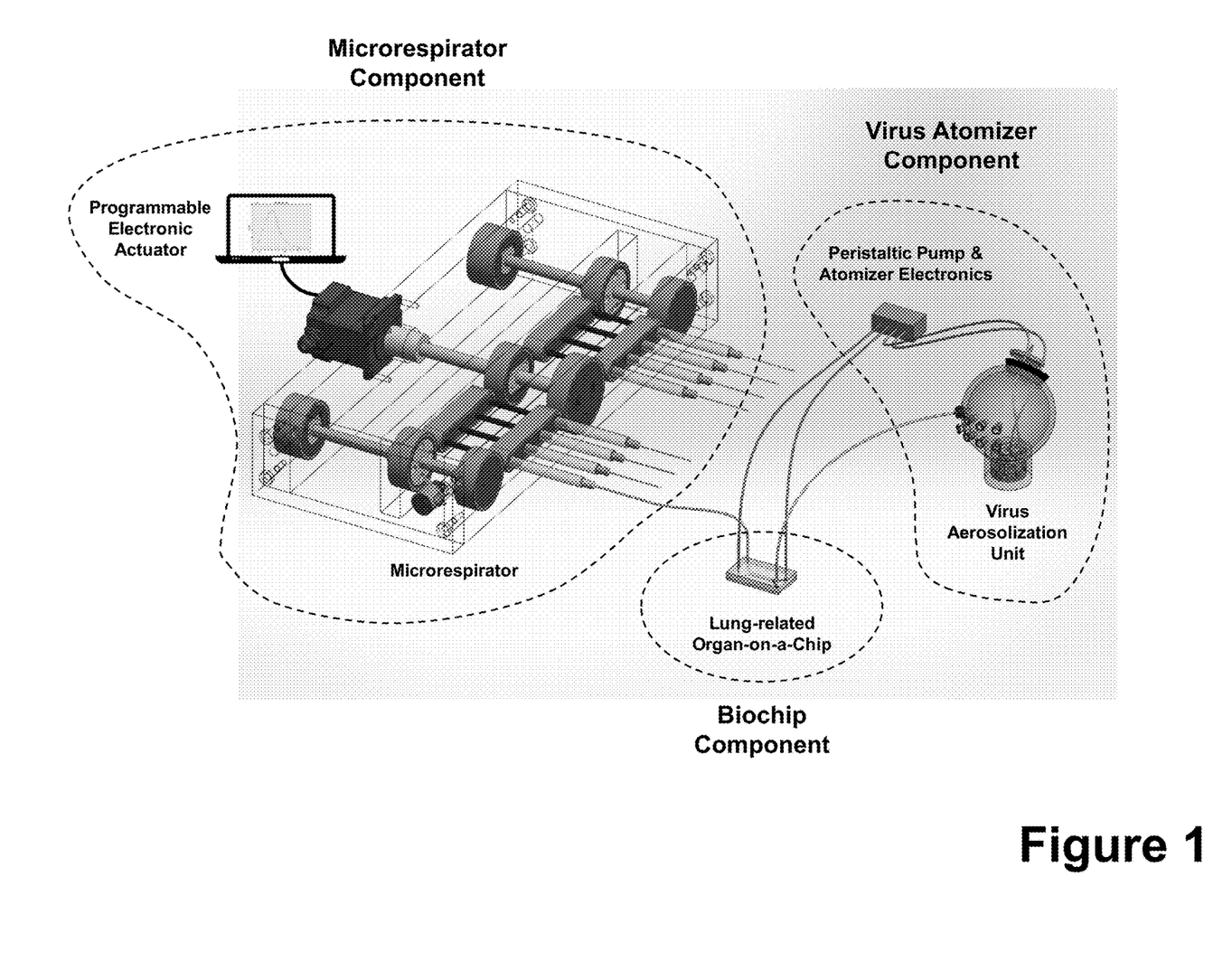
FIG. 1: A Novel System for Dynamic and Finely Regulated Inhaled Delivery of Aerosolized Respiratory Pathogens Without Disturbing Natural Air-Liquid Interface. The three major components of this system are (1) a microrespirator and its associated programmable electronic actuator that can translate displacement of gas-tight syringe plungers into breathing-mimicking movement of microliter precise volumes of air +/− aerosolized pathogens, (2) a biochip, which is a Lung-related Organ-on-a-Chip, that contains an airway lumen lined with primary mucociliated human lung airway epithelial cells for exposure to inhaled material, and (3) a virus atomizer to generated fresh microdroplets of a given respiratory pathogen (e.g., influenza virus) for challenging living cells.

In our studies, the biochip models the human small airway, which is an improved design of Small Airway-on-a-Chip. The atomizer chamber reproduces infectious bioaerosols and is completely new and novel, and the microrespirator replicates human breathing cycles. By combing all three components, we have created a system that "breathes" infectious aerosols into the human small airways (FIG. 1). The three key novel aspects here are (1) the 'virus atomization chamber', (2) the method for inhalation exposure of lung cells in vitro or ex vivo to aerosolized pathogens without disrupting natural ALI, and (3) the improved microrespirator-controlling software that enables generating breathing cycles (volume as function of time) from any desired (clinically relevant) Flow-Volume Curve.

Previous groups have used collision nebulizers to generate infectious aerosols. While, this system maintains air-liquid interface during infection, it passes the aerosols through a large chamber at high speeds (20 L/min) and requires passive the aerosols to settle on plates of cells. The virus delivery system described here improves upon the previous systems by also allowing aerosolization of virus on a smaller scale as well as incorporating physiologically relevant breathing into the exposure system.

Below is a detailed description of the components of our invention:

A—Virus Atomizer

Figure 2:
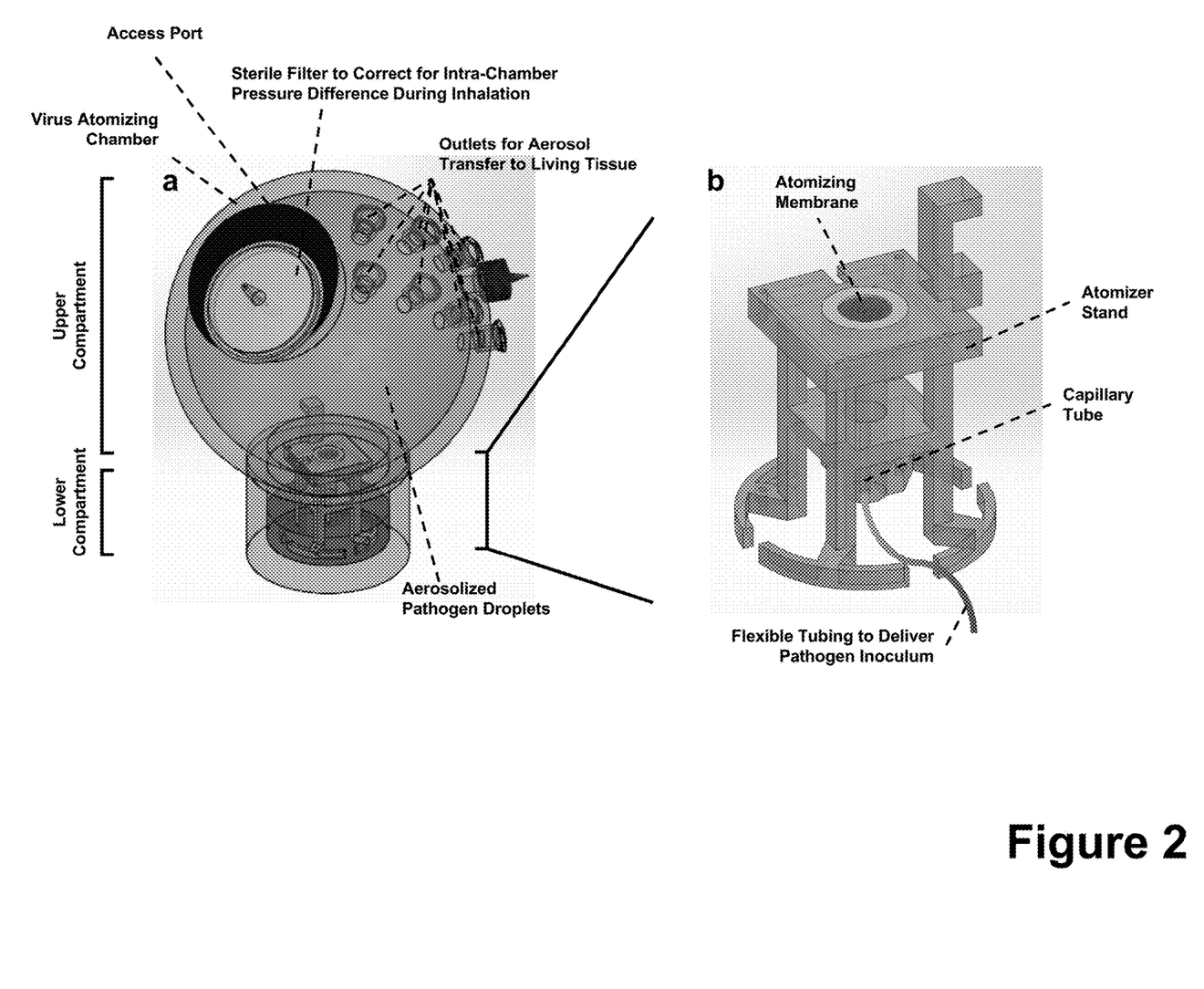
FIG. 2: Virus Atomizer. Descripting illustrations of our virus aerosolization chamber (a), and the atomizing membrane-housing stand (b) which sits inside the lower compartment of the chamber.

A 3D-printed biocompatible enclosure (chamber) (FIG. 2a) houses an electronically controlled piezoelectric atomizer (purchased from STEMiNC [STEINER & MARTINS, INC.]; catalogue #: SMMOD10F190), which sits over a support stand (FIG. 2b). We ran this atomizer at resonant frequency of 190 KHz so that once the liquid inoculum is brought in contact with the atomizer, it is converted to an aerosol with an average droplet size of 5 µm. Published reports have found that bioaerosols of 5 µm or less are a significant mode of transmission for respiratory pathogens like influenza virus. The stand is designed so that it has an open top configuration for the atomizing membrane to fit in securely and stabilize, while enabling efficient generation and ejection of (pathogen-containing) aerosols atop into the upper compartment of the chamber. The virus chamber contains a small reservoir at its base (lower compartment) where the stand is set into and the liquid inoculum can accumulate. Below the atomizer is a hollow shaft that holds a capillary tube attached to a microscale-inner-diameter flexible polymer tubing that deliver the pathogen (e.g., virus) liquid inoculum to the atomizing membrane. The flexible tubing is connected to reservoir via a peristaltic pump that on hand delivers the inoculum for aerosolization and on the other hand transfers unused and accumulated inoculum back to the reservoir until it is used up for the duration of experiment. In our studies, we used a commercially available peristaltic pump (purchased from Cole Parmer; catalogue #: EW-78001-32) at a flow rate of 30 µl per minute for 90 min. In addition, to simulate pathogenic aerosolization instead of a live microbe we used 200-nm fluorescent beads (which in terms of size are very similar to a respiratory virus).

The chamber contains one large opening known as the access port, where the atomizer stand and peristaltic pump tubing can be inserted. The opening is sealed using a rubber stopper. The rubber stopper allows sealing of the opening while still permitting tubing to get into the chamber. The rubber stopper has a hole bored into it which is filled with a Luer Lock needle connected to an air filter with 0.2 µm pores. The air filter serves as a vent for the system to prevent any pressure build-up. The virus chamber also contains a panel of 8 sample ports to connect to biochips. The sample ports have female Luer Lock threading, which can either be closed of via male Luer Lock caps or connected to biochip samples through a male Luer Lock tube adapter.

The virus chamber was created to have these three key design elements: (1) a reservoir (lower compartment) to collect the accumulated liquid inoculum and hold the atomizer support stand; (2) a hollow, unobstructed space into which freshly generated aerosols can fly into (upper compartment); and (3) samples ports to connect to the biochips. The shape of the main virus chamber (upper compartment) was created as a sphere-like to allow unobstructed air movement and to allow any condensing aerosolized droplets to return to the liquid reservoir at the base. The sample ports were created with universal Luer threading to allow maximum adaptability.

Figure 3:
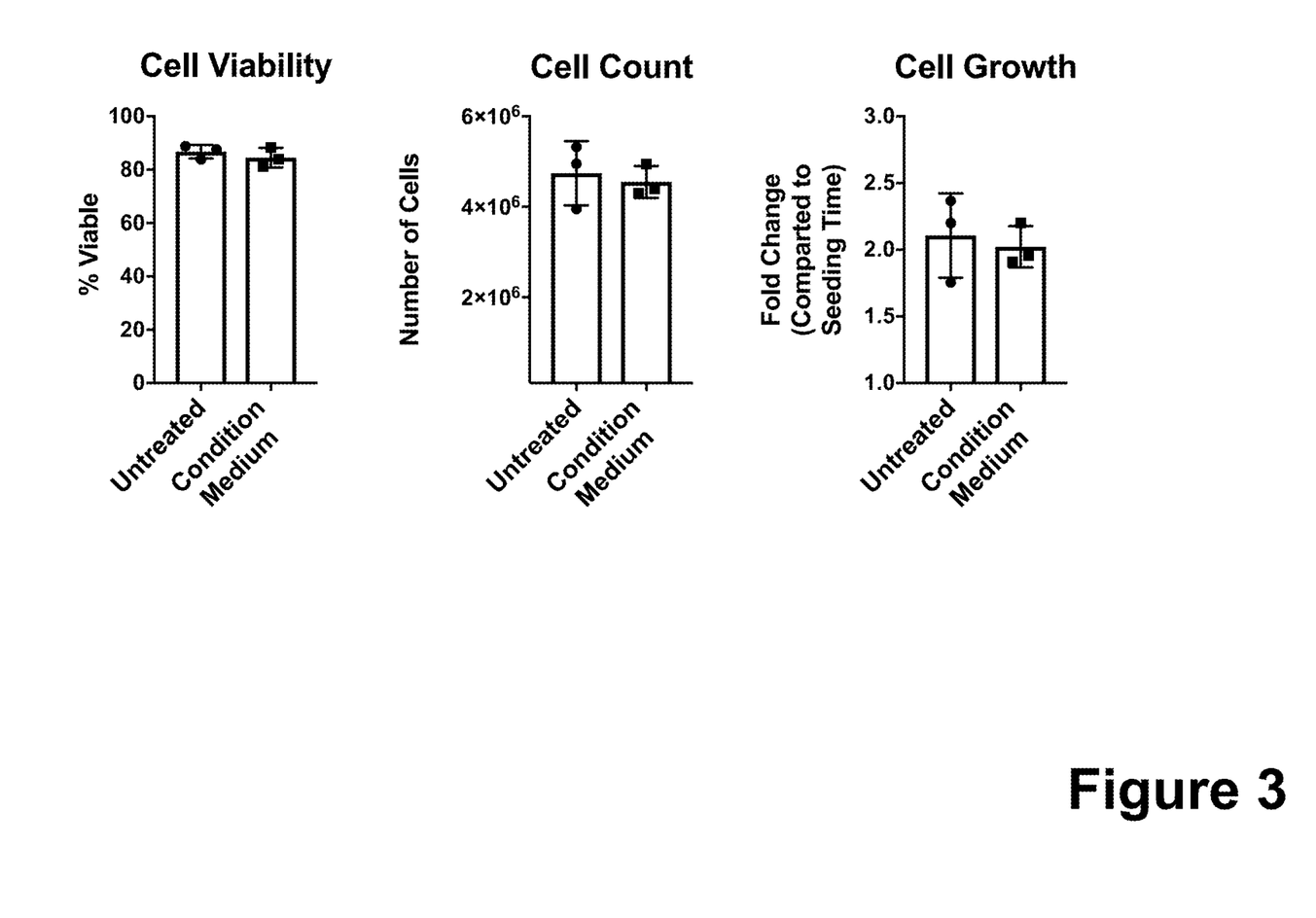
FIG. 3: VeroClear Does Not Alter Viability and Growth of Living Cells. The virus chamber was rinsed with DMEM for 30 minutes. 293T cells were cultured 72 hours in either fresh DMEM medium or the conditioned medium from the virus chamber. Viability was measured by Trypan blue staining. Fold growth was calculated by dividing the number of cells recovered after 72 hours of culture by the number of cells plated.

The chamber was 3D printed using VeroClear as build-material. To ensure this material does not negatively impact or contaminate condensed viral particles that get re-aerosolized for exposure, we incubated the inner surface of the chamber with culture medium DMEM for 30 min and used this conditioned medium to challenge 293T cells for 72 hrs. Next, we assessed viability/cytotoxicity (by Trypan blue staining) and quantified the cell numbers and fold-change in growth between 293T cells stimulated with VeroClear-conditioned medium and untreated 293T cells. As shown in FIG. 3, no significant difference was identified indicating that it is unlikely that the material used for creating the atomization chamber would have any negative impact on biological material in terms of growth and toxicity.

B—Microrespirator

Figure 4:
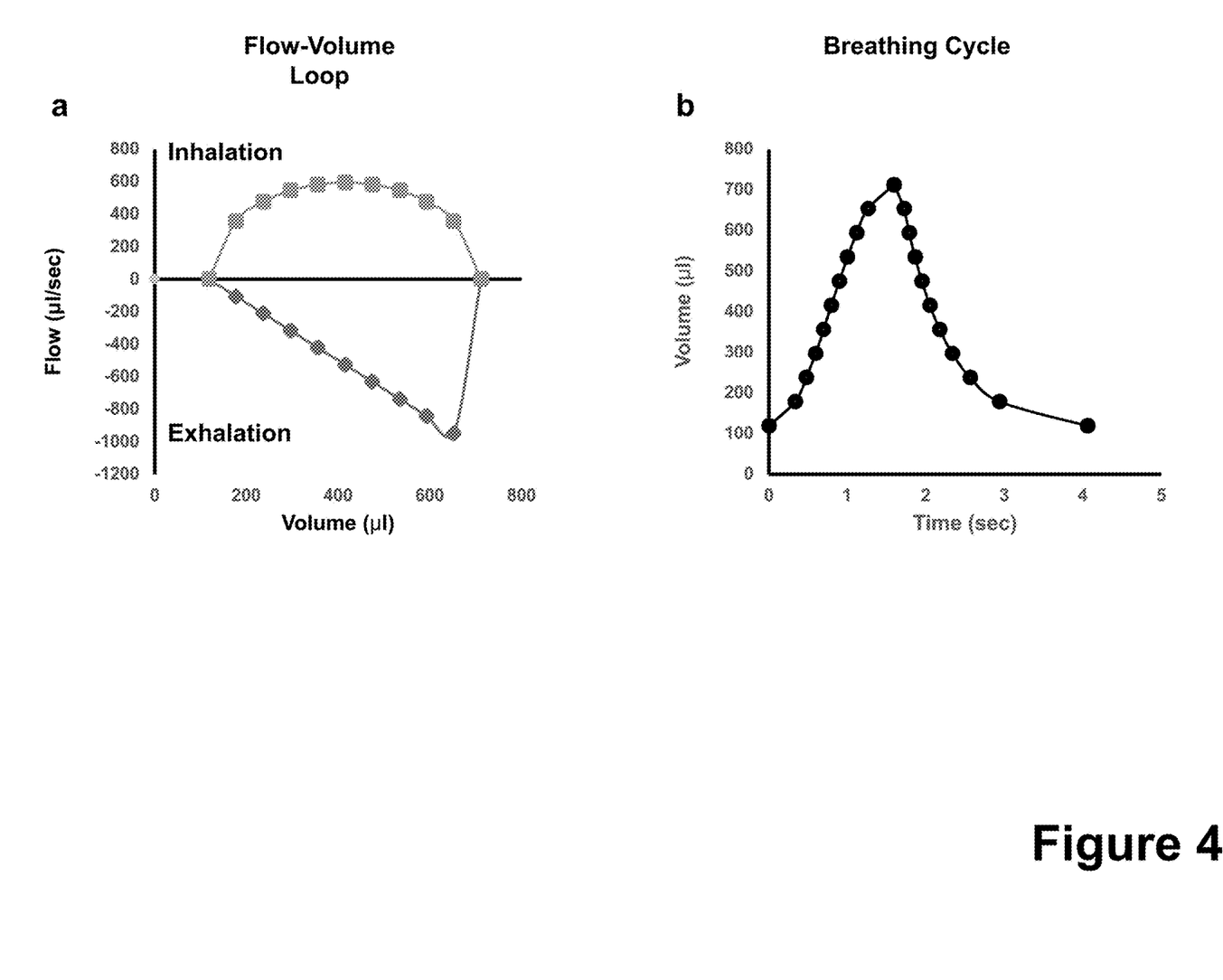
FIG. 4: Breathing Profile for Inhaled Exposure to Aerosolized Pathogen. The software that actuated microrespirator can be provided with any desired flow-volume loop (a) and convert it into flow-volume curve (b) to drive the instrument.

The microrespirator is a pneumatic extruder system that creates physiologically relevant rhythmic breathing cycles by extruding and aspirating air via plungers of gas tight syringes that moves back and forth (FIG. 1, left component). As the plungers are actuated, their translocation translates into displacement of air and as such they induce airflow over the cells in the biochip and within the virus chamber. The speed and timing of the plungers is controlled by an Arduino board such that the airflow within the system mimics the natural breathing cycle of a human (FIG. 4). It is a common practice to measure and characterize breathing based off of Flow-Volume Loops, which can demonstrate healthy breathing along with obstructions and breathing disorders. A custom MATLAB script generates profiles related to the targeted breathing cycle as Flow-Volume Loops, which are then converted into volume profiles as a function of time. This is accomplished through treating the generated graph as a set of non-linear first order differential equation and performing numerical analysis on the Flow-Volume Loop to generate the volume as a function of time. The algorithm then utilizes characteristics of the microrespirator and targeted airway channel diameter of the biochip to generate two sets of data describing number of motor steps and step rates which drive the micro-respirator to produce the physiologically relevant breathing profile. Here we have improved the MATLAB script so that they can be fed with any given Flow-Volume Loops and in return generate Volume-Time Breathing Cycles (FIG. 4).

C—Biochip

Here we used Advanced Lung Airway Organomimetic Device. Organ-on-chips are biomimetic, microfluidic, cell culture devices created with microchip manufacturing methods that contain continuously perfused hollow microchannels inhabited by living tissue cells arranged to simulate organ-level physiology. By recapitulating the multicellular architectures, tissue-tissue interfaces, chemical gradients, mechanical cues, and vascular perfusion of the body, these devices produce levels of tissue and organ functionality not possible with conventional 2D or 3D culture systems. They also enable high-resolution, real-time imaging and in vitro analysis of biochemical, genetic and metabolic activities of living human cells in a functional human tissue and organ context.

We have previously engineered organ-on-chip microdevices that reproduce several key structural and functional of human lung small airways. The lead device design was called 'Human Lung Small Airway-on-a-Chip'. However, it this format it had two major limitations: (1) the cross-section of the airway lumen channel unlike what is observed in our lungs, is square-shaped with sharp edges; this can impact the airflow and inhalation exposure studies where air/gas/smoke shear could be important in basic physiology or pathology development; and (2) the porous membrane on which the cells are seeded is 1000 micrometers; based on our experience such width causes (i) membrane sagging into the underlying vascular channel, and (ii) creates a non-homogenously ciliated cell coverage in the epithelium; these two can in turn affect vascular shear stress (by disturbing the medium/blood flow), and mucociliary transport and cilia synchronization.

Figure 5:
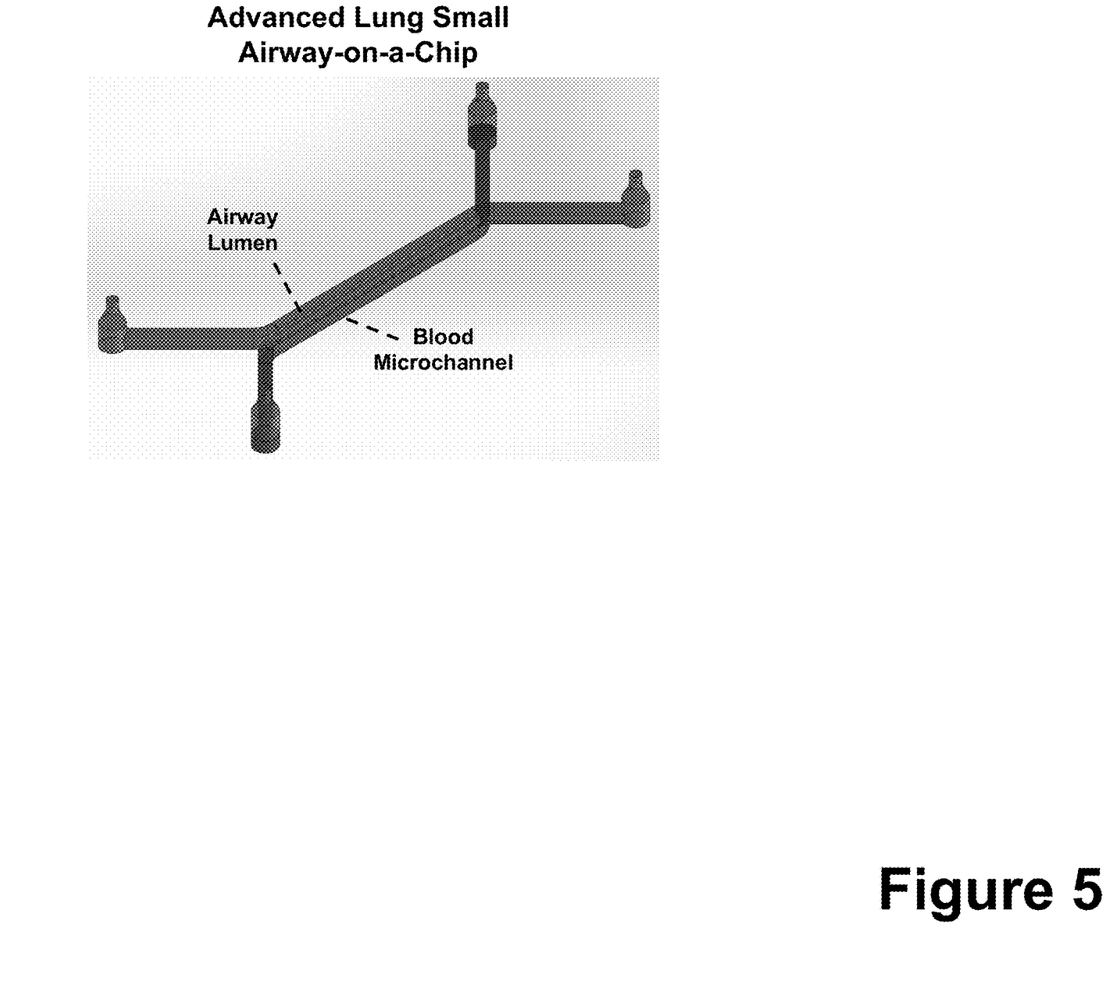
FIG. 5: Biochip. Graphic illustrations of the Advanced Lung Small Airway Chip we used in our studies.

To tackle these challenges, we designed an Advanced Lung Small Airway-on-a-Chip device (FIG. 5) that compared with the earlier prototype described above offers these key advantages: (1) its airway lumen channel is more in vivo-like and is almost circular on its cross-section, as opposed to square-shaped design of our earlier prototype; and (2) it has a narrower membrane width (~500 micrometers instead of 1000 micrometers). These features enable more physiological relevance for airflow/breathing/inhaled exposure, and better tissue-level synchrony of the cilia (tighter packing and proximity of ciliated cells would support planar cell polarity.

Figure 6:
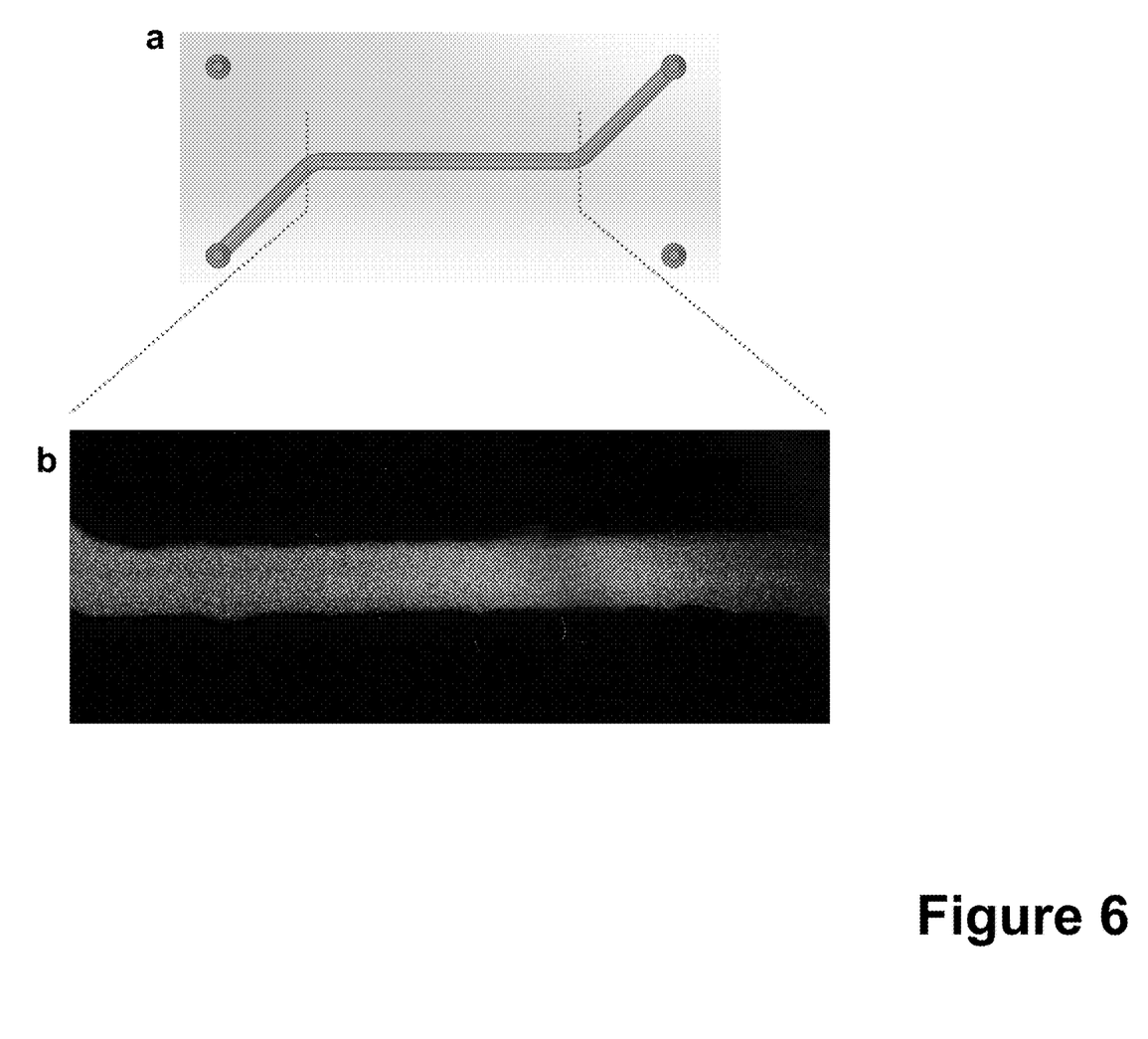
FIG. 6: Inhalation Exposure to Fluorescently Tagged Beads On-Chip. The top compartment of the Small Airway Chip (a) mounted on a glass slide exposed to 200-nm beads for 90 min under physiological breathing (FIG. 4b) showed extensive and uniform coverage of the central channel area (where mucociliated airway epithelial cells normally grow) to the beads (b).

For studies here, we mounted the top compartment of the device, which contains the 'airway lumen' feature, over a glass cover slip so that we can clearly demonstrate inhalation of fluorescently tagged microparticles—to represent a given pathogenic sample, into the chip. One end of the airway lumen was connected via flexible tubing to the microrespirator and the other end to the virus atomization chamber. Following physiological breathing (FIG. 4) for 90 min, we observed successful and a highly uniform distribution of the beads along the central area of the airway lumen channel, in an area that mucociliated airway epithelial cells occupy in fully mature biochip (FIG. 6)

Variations and Optional Features

Many different pathogens, including but not limited to viral, bacterial, fungal and yeast, may be aerosolized using our platform;

Our System can be used to aerosolize pharmaceuticals or any type of inhalable molecule/compound;

The size of the virus chamber may be increased or decreased;

Air filters with different pore sizes based on the pathogen/aerosol size may be used;

The number of sample access ports can be increased or decreased;

Atomizers of different sizes, properties and frequencies may be used;

The average droplet size of the aerosol produced can be increased or decreased;

The pump delivery of liquid inoculum to atomizer is not limited to a peristaltic mechanism and can be any other pumping/circulatory platform;

The biochip sample can be larger or smaller;

Other in vitro or ex vivo systems may be used instead of biochip;

The biochip can be populated by cells other than small airway epithelial and endothelial cells;

The breathing profiles actuated by the micro-respirator can include healthy breathing as well as diseased breathing patterns such as patients with asthma, chronic obstructive pulmonary disease (COPD), cystic fibrosis, pneumonia, or any other user-defined profile.

A system that generates aerosol infectious agents for inhaled exposure to the lung tissue under physiological breathing and without disturbing natural ALI that exists in the lung;

Enabling simultaneous infection of multiple biochips (or any relevant biological systems) at once;

A new platform (Virus Atomization Chamber) for creating aerosolized pathogenic droplets;

An improved microrespirator-controlling software that enables generating breathing cycles (volume as function of time) from any desired (clinically relevant) Flow-Volume Curve.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure.

The scope of the disclosure accordingly may be limited by the appended claims, in which reference to an element in the singular is not intended to mean "one and only one" unless explicitly so stated, but rather "one or more." It is to be understood that unless specifically stated otherwise, references to "a," "an," and/or "the" may include one or more than one and that reference to an item in the singular may also include the item in the plural. All ranges and ratio limits disclosed herein may be combined.

Moreover, where a phrase similar to "at least one of A, B, and C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

The steps recited in any of the method or process descriptions may be executed in any order and are not necessarily limited to the order presented. Furthermore, any reference to singular includes plural embodiments, and any reference to more than one component or step may include a singular embodiment or step. Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

Any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts or areas but not necessarily to denote the same or different materials. In some cases, reference coordinates may be specific to each figure.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

The invention claimed is:

1. A system comprising:
a respirator configured to create breathe-mimicking air movement;
a biochip comprising an airway lumen in fluid communication with the respirator; and
an atomizer comprising:
a housing comprising:
a lower compartment defining a reservoir for liquid inoculum;
a sphere-shaped upper compartment defining a volume for generated aerosols;
at least one sample port for fluidly connecting the upper compartment to at least one of the biochip and the respirator; and
a support stand disposed in the lower compartment and partially submerged in the liquid inoculum;
an atomizing membrane disposed between the lower compartment and the upper compartment;
wherein the support stand supports the atomizing membrane above the liquid inoculum;
a pump; and
a tube connected to the reservoir and the pump;
wherein the pump is configured to deliver the liquid inoculum from the reservoir to the atomizing membrane and transfer unused liquid inoculum back to the reservoir;
wherein the respirator and the atomizer are in fluid communication with the airway lumen of the biochip; and
wherein the respirator is in fluid communication with the atomizer.

2. The system of claim 1, wherein the atomizer is configured to generate droplets of a respiratory pathogen.

3. The system of claim 1, wherein the breath-mimicking air movement comprises air volume as a function of time, wherein the respirator is configured to generate breathing cycles.

4. The system of claim 1, wherein the respirator is a pneumatic extruder comprising at least one syringe, wherein the at least one syringe comprises a plunger configured to translate linearly to produce the breathe-mimicking air movement.

5. The system of claim 1, wherein the airway lumen of the biochip is lined with primary mucociliated human lung airway epithelial cells.

6. The system of claim 1, wherein the biochip comprises a plurality of continuously perfused hollow microchannels inhabited by living tissue cells arranged to simulate organ-level physiology.

7. The system of claim 1, wherein the airway lumen of the biochip comprises a circular cross-section.

8. The system of claim 7, wherein the biochip further comprises a vascular channel and a membrane disposed between the airway lumen and the vascular channel.

9. The system of claim 8, wherein a width of the membrane is less than 1,000 micrometers.

10. The system of claim 8, wherein a width of the membrane is less than 500 micrometers.

11. The system of claim 1, wherein a first end of the airway lumen of the biochip is coupled to the respirator and a second end of the airway lumen of the biochip is coupled to the atomizer.

12. The system of claim 1, wherein the atomizer comprises an atomizing membrane, such as an electronically actuated piezoelectric atomizer.

13. The system of claim 1, wherein the tube comprises a capillary tube attached to a microscale-inner-diameter flexible polymer tubing.

14. The system of claim 1, wherein the upper compartment defines an access port through which the support stand may be inserted.

15. The system of claim 1, wherein the atomizer further comprises an air filter configured to vent the system.

16. The system of claim 1, wherein the pump is a peristaltic pump.

17. The system of claim 1, wherein the respirator induces airflow over the biochip and within the atomizer.

* * * * *